United States Patent
Knepper et al.

(10) Patent No.: US 11,723,343 B2
(45) Date of Patent: Aug. 15, 2023

(54) SYSTEM AND METHOD FOR IN OVO SEXING OF AVIAN EMBRYOS

(71) Applicant: NOVATRANS GROUP S.A., Corcelles (CH)

(72) Inventors: Paul Knepper, Austin, TX (US); Matthew O'Hayer, Austin, TX (US); Jonathan Hoopes, Austin, TX (US); Eran Gabbai, Maas (IL)

(73) Assignee: NOVATRANS GROUP S.A., Corcelles (CH)

( * ) Notice: Subject to any disclaimer, the term of this patent is extended or adjusted under 35 U.S.C. 154(b) by 5 days.

(21) Appl. No.: 17/217,884

(22) Filed: Mar. 30, 2021

(65) Prior Publication Data
US 2021/0212296 A1    Jul. 15, 2021

Related U.S. Application Data

(62) Division of application No. 16/321,261, filed as application No. PCT/US2017/044609 on Jul. 31, 2017, now Pat. No. 11,006,617.

(Continued)

(51) Int. Cl.
*G01N 33/08* (2006.01)
*A01K 43/00* (2006.01)
(Continued)

(52) U.S. Cl.
CPC .............. *A01K 43/00* (2013.01); *A01K 43/04* (2013.01); *A01K 45/00* (2013.01); *A61B 10/00* (2013.01);
(Continued)

(58) Field of Classification Search
CPC ............... G02N 33/085; G01N 21/255; G01N 2201/061; G01N 2201/0438
See application file for complete search history.

(56) References Cited

U.S. PATENT DOCUMENTS 4,594,226 A    6/1986  Reedy
4,671,652 A    6/1987  Van Asselt et al.
(Continued)

FOREIGN PATENT DOCUMENTS

CN    101419212    4/2009
CN    103808595    5/2014
(Continued)

OTHER PUBLICATIONS

Cheng et al., "Terahertz biosensing metamaterial absorber for virus detection based on spoof surface plasmon polaritons", International Journal of RF and Microwave Computer-Aided Engineering, May 2018, pp. 1-7, 2018 Wiley Periodicals Inc.
(Continued)

*Primary Examiner* — Don K Wong
(74) *Attorney, Agent, or Firm* — Tarolli, Sundheim, Covell & Tummino L.L.P.

(57) ABSTRACT

A system for determining the gender and/or fertility status of avian eggs including a sampling apparatus and an electromagnetic radiation transmitter and detector. In certain embodiments, the transmitter operates in the terahertz range. The sampling apparatus can be coupled to an avian egg. The sampling apparatus includes a vacuum source, a gas collection device, and a membrane that can be positioned in the passageway coupling the vacuum source to the gas collection device. The membrane is capable of capturing volatile organic compounds. The sampling apparatus applies a vacuum from the vacuum source to the gas proximate to the avian egg and directs the gas captured from the vicinity of the egg toward the membrane. Subsequently, the membrane is positioned within the electromagnetic radiation emitted by the transmitter, generating a spectrum which can be analyzed to determine whether the egg is fertile or infertile, and if fertile, whether the egg is male or female. In an embodi-
(Continued)

ment, the captured volatile organic compounds are transferred to a sample chamber where the captured gas is analyzed.

17 Claims, 4 Drawing Sheets

Related U.S. Application Data

(60) Provisional application No. 62/368,623, filed on Jul. 29, 2016.

(51) Int. Cl.
| | |
|---|---|
| *A01K 45/00* | (2006.01) |
| *G01N 21/3504* | (2014.01) |
| *G01N 1/22* | (2006.01) |
| *G01N 21/3581* | (2014.01) |
| *A01K 43/04* | (2006.01) |
| *A61B 10/00* | (2006.01) |

(52) U.S. Cl.
CPC ............ *G01N 1/22* (2013.01); *G01N 1/2214* (2013.01); *G01N 1/2226* (2013.01); *G01N 21/3504* (2013.01); *G01N 21/3581* (2013.01); *G01N 33/08* (2013.01); *A61B 2010/0083* (2013.01); *A61B 2503/40* (2013.01)

(56) References Cited

U.S. PATENT DOCUMENTS

| | | | |
|---|---|---|---|
| 4,955,728 | A | 9/1990 | Hebrank |
| 5,983,830 | A | 11/1999 | Cox et al. |
| 9,279,723 | B2 | 3/2016 | Roulston et al. |
| 2003/0185422 | A1 | 10/2003 | Taniguchi |
| 2004/0107912 | A1 | 6/2004 | Hebrank |
| 2009/0091742 | A1 | 4/2009 | Hebrank et al. |
| 2010/0086750 | A1 | 4/2010 | Blumberg et al. |
| 2013/0023040 | A1 | 1/2013 | Phelps et al. |
| 2014/0283626 | A1 | 9/2014 | McMurtry et al. |
| 2015/0138535 | A1* | 5/2015 | Walukas ............ G01N 33/085 356/51 |
| 2015/0145435 | A1 | 5/2015 | Ogawa |
| 2016/0050891 | A1 | 2/2016 | Phelps et al. |
| 2019/0174726 | A1 | 6/2019 | Knepper et al. |

FOREIGN PATENT DOCUMENTS

| | | |
|---|---|---|
| CN | 204028046 | 12/2014 |
| CN | 105101786 | 11/2015 |
| CN | 108211807 A | 6/2018 |
| CN | 110487751 A | 11/2019 |
| DE | 10 2012 023 947 A1 | 6/2014 |
| JP | 2003-274791 A | 9/2003 |
| JP | 2006-105646 A | 4/2006 |
| JP | 2006-145512 A | 6/2006 |
| JP | 2011-242180 A | 12/2011 |
| JP | 2012-231700 A | 11/2012 |
| JP | 2016-538550 A | 12/2016 |
| JP | 2018-169165 A | 11/2018 |
| JP | 2019-523019 A | 8/2019 |
| WO | WO-2011/143349 A1 | 11/2011 |
| WO | WO-2014/086335 A1 | 6/2014 |
| WO | WO-2015/074008 A1 | 5/2015 |
| WO | WO-2015/145435 A1 | 10/2015 |
| WO | WO-2018/023105 A1 | 2/2018 |
| WO | WO-2019/021275 A1 | 1/2019 |

OTHER PUBLICATIONS

Maier et al., "Toward Continuous Monitoring of Breath Biochemistry: A Paper-Based Wearable Sensor for Real-Time Hydrogen Peroxide Measurement in Simulated Breath", ACS Sensors, 2019, pp. 2945-2951, vol. 4, American Chemical Society.
Rothbart et al., "Analysis of Human Breath by Millimeter-Wave/ Terahertz Spectroscopy", Sensors, 2019, pp. 1-12, vol. 19, No. 2719.
Rothbart et al., "Towards Breath Gas Analysis Based on Millimeter-Wave Molecular Spectroscopy", Frequenz, 2018, pp. 87-92, vol. 72, Nos. 3-4.
Sareen et al., "IoT-based cloud framework to control ebola virus outbreak", Journal of Ambient Intelligence and Humanized Computing, Oct. 20, 2016, 18 pages, Springer.
Van Der Schee et al., "Altered exhaled biomarker profiles in children during and after rhinovirus-induced wheeze", European Respiratory Journal, 2015, pp. 440-448, vol. 45.
Alessandra Costanzo et al., "The Odour of Sex: Sex-Related Differences in Volatile Compound Composition among Barn Swallow Eggs Carrying Embryos of Either Sex", PLOS ONE, Nov. 16, 2016, pp. 1-17, vol. 11, No. 11.
Ben Webster et al., "Avian Egg Odour Encodes Information on Embryo Sex, Fertility and Development", PLOS ONE, Jan. 28, 2015, pp. 1-10, vol. 19, No. 1.
Konstantinos I. Diamantaras et al., "Principal Component Neural Networks: Theory and Applications." Wiley-Inter-science, New York, 1996 (Book Review), 1998 Springer-Verlag London Limited.
Notice of Allowance on U.S. Appl. No. 16/321,261 dated Dec. 30, 2020.
OSA Publishing Co., "Terahertz Volatile Gas Sensing by Using Polymer Microporous Membranes", https://www.osapublishing.org, pp. 1-19 (2020).
P. C. Mahalanobis, "On the generalized distance in statistics.", Proceeding of the National Institute of Sciences of India, Apr. 15, 1936, pp. 49-55, vol. II, No. 1.
R. A. Fisher, "The Use of Multiple Measurements in Taxonomic Problems", Annals of Eugenics, 7 Part II, 1936, pp. 179-188.
You et all., "Terahertz Volatile Gas Sensing by Using Polymer Microporous Membranes", Optics Express, vol. 23, No. 3, p. 2048, Jan. 26, 2015.
Liang et al., "Detection of Gases with Terahertz Spectroscopy Techniques," Laser and Optoelectronics Progress, pp. 29-40, Jul. 2009.

* cited by examiner

SYSTEM AND METHOD FOR IN OVO SEXING OF AVIAN EMBRYOS

CROSS-REFERENCE TO RELATED APPLICATIONS

The present application is a divisional of U.S. patent application Ser. No. 16/321,261, filed on Jan. 28, 2019, which is national stage entry of International Patent Application No. PCT/US2017/044609, filed on Jul. 31, 2017, which claims priority to and the benefit of U.S. Provisional Application No. 62/368,623, filed on Jul. 29, 2016, the contents of which are hereby incorporated by reference in their entirety.

BACKGROUND OF THE INVENTION

1 Field of the Invention

The invention generally relates to the in ovo gender determination and fertility verification of avian embryos. More specifically, the invention relates to rapid multiple egg in ovo gender and fertility determination in a commercial setting.

2. Description of the Relevant Art

In commercial poultry production, one gender may be selected over another for various practical and economic reasons. For the production of table eggs, females are selected for their ability to lay eggs, and males and infertile eggs are culled. In the case of broilers, males and females are often separated due to their different growth rates and time to maturity, making it more economical to raise and feed them separately.

In order to determine sex, trained human sexers are used to identify the bird's gender within a day of hatching, usually by feather length or via cloacal anatomy. Culling of the unwanted gender often takes place via maceration or suffocation. The waste product from the culled chicks is then disposed of, often at additional cost to the hatchery. Because the birds must first be hatched in order to have their gender identified, hatcheries require twice the incubation and hatching capacity needed to produce a given number of female laying hens (the sex ratio being roughly 50:50 male to female) or male broilers.

While known art has been proposed for in ovo sexing, these techniques are invasive, requiring puncturing the shell and membranes, to either remove a sample (e.g., of the blastoderm) or gain entry to directly illuminate (in the case of spectrometric techniques) egg components containing genetic material or other bio-identifying molecules and proteins. In addition to invasiveness, the aforementioned techniques rely on measuring phenomena such as differences in the mass of genetic material, feather coloring, sex-linked proteins, nucleotides, and the like, or differences in sex hormones. In all cases these identifiers emerge only after several days of incubation, requiring hatcheries to maintain enough capacity for these additional eggs. In a similar manner, using the aforementioned techniques, infertile eggs must be incubated for some time before lack of embryo development is evident.

Identifying a bird's gender in ovo would enable hatcheries to reduce incubation and hatchery operations and eliminate labor-related sexing costs, resulting in gains in productivity and efficiency for the plant. The earlier eggs with relevant traits can be identified, the sooner they can be segregated (e.g., in the case of broilers) or culled (e.g., in the case of laying hens). This creates the maximum economic benefit to the hatchery by limiting the amount of time eggs that are destined for separation or culling must be incubated. The solutions mentioned in the prior art require at least some incubation before the egg can be properly identified and handled. Thus, there is need in the market for a solution that can identify the gender or fertility of an egg non-invasively and before an egg requires incubation.

SUMMARY OF THE INVENTION

In an embodiment, a system for determining the gender and/or fertility status of avian eggs includes a sampling apparatus and an electromagnetic radiation transmitter and detector. The transmitter may operate in, in various embodiments, the terahertz range, the microwave range, or the infrared range. The sampling apparatus can be coupled to an avian egg. The sampling apparatus includes a vacuum source, a gas collection device, and a membrane that can be positioned in the passageway coupling the vacuum source to the gas collection device. The membrane is capable of capturing volatile organic compounds. The sampling apparatus applies a vacuum from the vacuum source to the gas proximate to the avian egg and directs the gas captured from the vicinity of the egg toward the membrane. Subsequently, the membrane is positioned within the electromagnetic radiation emitted by the transmitter.

In an embodiment, a method of determining the gender and/or fertility status of avian eggs includes: coupling a sampling apparatus to an avian egg, in which the sampling apparatus includes a vacuum source, a gas collection device, and a membrane capable of capturing volatile organic compounds; operating the sampling apparatus to capture gas proximate to the avian egg via the gas collection device, in which the sampling apparatus directs the captured air toward the membrane; and applying electromagnetic radiation to the membrane, and in which the electromagnetic radiation is preselected to allow the quantity of one or more volatile organic compounds captured in the membrane to be determined.

In an embodiment, a system for determining the gender and/or fertility status of avian eggs includes a sampling apparatus and an electromagnetic radiation transmitter and detector. The sampling apparatus applies a vacuum from the vacuum source to the gas proximate to the avian egg and directs the gas captured from the vicinity of the egg toward a sample chamber. The sample chamber is positioned within the electromagnetic radiation emitted by the transmitter.

In an embodiment, a method of determining the gender and/or fertility status of avian eggs includes: coupling the sampling apparatus to the avian egg; operating a sampling apparatus to capture gas proximate to the avian egg via the gas collection device, in which the sampling apparatus directs the captured gas into the sample chamber; and applying electromagnetic radiation to the sample chamber, in which the electromagnetic radiation is preselected to allow the quantity of one or more volatile organic compounds captured in the sample chamber to be determined.

In an embodiment, a system for determining the gender and/or fertility status of avian eggs includes one or more carriers for receiving one or more avian eggs, one or more transmitters capable of emitting preselected electromagnetic radiation, and one or more detectors. The transmitters direct the preselected electromagnetic radiation into the one or more avian eggs. As a non-exhaustive example, tunable continuous wave terahertz radiation (CW-THz) can be generated via photomixing techniques known in the art using two Ti:sapphire lasers in adjacent wavelengths to generate a beat frequency in the desired range. Numerous antennae arrays are available for emitting the terahertz radiation, often consisting of GaAs structures. Many variations exist in the particulars of creating terahertz (and other spectrum) radiation; a suitable device may be used that most efficiently produces the desired waveband. The detectors are capable of detecting the preselected electromagnetic radiation that passes through the one or more avian eggs using proper antennae, electro-optical sampling methods, or other suitable techniques.

In an embodiment, a method of determining the gender and/or fertility status of avian eggs includes: positioning the air sac of an egg in the optical pathway between a transmitter and a detector; and applying electromagnetic radiation to the air sac of the egg through the unbroken shell, in which the electromagnetic radiation is preselected to allow the quantity of one or more organic compounds in the air sac of the egg to be determined.

BRIEF DESCRIPTION OF THE DRAWINGS

Advantages of the present invention will become apparent to those skilled in the art with the benefit of the following detailed description of embodiments and upon reference to the accompanying drawings in which.

Figure 6:
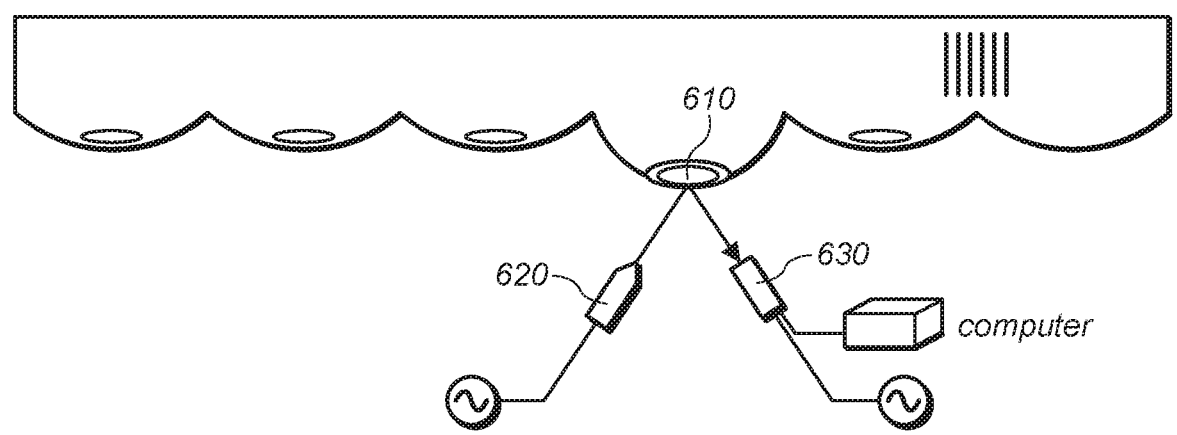
FIG. 6 depicts a schematic diagram of an exemplary in ovo detection system whereby the air sac is in the bottom position, requiring the spectrometer to be placed beneath the eggs, and special trays allowing the area of the egg containing the air sac to be exposed to the spectrometer.

While the invention may be susceptible to various modifications and alternative forms, including reversing the position of the vacuum to the bottom of the egg when the egg is oriented with the air sac facing down, e.g. using trays like that depicted in FIG. 6, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims. For example, though the drawings typically depict the egg with the air sac in the top position, if eggs are transported or moved about with the air sac in the bottom position, the invention allows for the apparatus to be reversed, with the vacuum collection taking place from the bottom of the egg (i.e., the location of the air sac in this example).

DETAILED DESCRIPTION OF ILLUSTRATIVE EMBODIMENTS

It is to be understood the present invention is not limited to particular devices or methods, which may, of course, vary. It is also to be understood that the terminology used herein is for the purpose of describing particular embodiments only, and is not intended to be limiting. As used in this specification and the appended claims, the singular forms "a", "an", and "the" include singular and plural referents unless the content clearly dictates otherwise. Furthermore, the word "may" is used throughout this application in a permissive sense (i.e., having the potential to, being able to), not in a mandatory sense (i.e., must). The term "include," and derivations thereof, mean "including, but not limited to." The term "coupled" means directly or indirectly connected.

As used herein the term "avian eggs" refers to the eggs obtained from avian species. Exemplary avian species include, but are not limited to, chickens, turkeys, ducks, quails, and geese.

Systems and methods disclosed herein addresses shortcomings of other methods of in ovo gender and fertility determination by measuring volatile organic compounds (VOCs) in the egg's air cell through the shell or in atmosphere (either directly or via a collecting membrane or via a collecting chamber), enabling non-invasive detection of gender and fertility status prior to incubation. These volatiles vary throughout the incubation period, and have been shown to differ between fertile and infertile eggs, as well as being predictive of embryo sex as early as day 1 of incubation. The type and quantity of typical VOCs emitted by avian eggs are discussed in the paper by Webster et al. "Avian Egg Odour Encodes Information on Embryo Sex, Fertility and Development" (2015) PLoS ONE 10(1): e0116345, and Costanzo et al, "The Odour of Sex: Sex-Related Differences in Volatile Compound Composition among Barn Swallow Eggs Carrying Embryos of Either Sex" (November 2016) PLOS ONE DOI:10.1371/journal.pone.0165055, both of which are incorporated herein by reference.

Eggs diffuse volatile organic compounds, as well as $CO_2$, $H_2O$, and $O_2$, readily through their pores. Up to 20 L of oxygen, carbon dioxide and water vapor can diffuse through the pores of an 80 gm egg by the time internal pipping takes place. These high vapor pressure volatiles can be detected using spectroscopic techniques.

Membrane System

In one embodiment, a system for determining the gender and/or fertility status of avian eggs includes a sampling apparatus that can be used to collect volatile organic compounds (VOCs) from an intact egg. In one embodiment, the sampling apparatus includes a vacuum source and a membrane capable of capturing volatile organic compounds. Any membrane capable of capturing VOCs of interest can be used. In one embodiment, a polyethylene terephthalate (PET) membrane is used. An exemplary polyethylene terephthalate membrane is described in U.S. Provisional Patent Application No. 62/326,857 entitled "Avian Gender Classification in Egg Prior to Hatch Using Chemical Indicators in THz spectrum", filed Apr. 25, 2016, which is incorporated herein by reference.

During use, a sampling apparatus applies a vacuum from the vacuum source to the gas proximate to the avian egg and directs the gas captured from the vicinity of the egg toward the membrane. In an embodiment, the sampling apparatus includes a gas collection device which is placed proximate to the egg. The gas collection device may have a number of shapes chosen to optimize the collection of VOCs from a single egg. In an embodiment, the gas collection device has a shape complementary to the shape of a single egg (e.g., is "egg shaped" or ovoid). In one embodiment, the gas collection device is the egg contact portion of a vacuum egg lifter.

In one embodiment, off-gassed VOCs are adsorbed onto the membranes. The "loaded" membranes are then analyzed by applying electromagnetic radiation (e.g., between 600-750 in the case of the terahertz part of the spectrum, though other bands of the electromagnetic spectrum may be used) to the membrane and observing the change in the electromagnetic radiation. Analysis of the membrane may be accomplished using an electromagnetic radiation transmitter and an electromagnetic radiation detector typical of a spectrometer operating at microwave, terahertz or infrared wavelengths. During analysis the membrane is positioned within the beam of electromagnetic radiation emitted by the transmitter. The electromagnetic radiation passes into the membrane and the interaction of the VOCs trapped in the membrane alter the electromagnetic radiation. After contacting the membrane, the altered electromagnetic radiation is captured by the electromagnetic radiation detector. The changes in the electromagnetic radiation can be used to determine what VOCs are being released by the egg. Male, female, fertile and infertile eggs all release a unique combination of VOCs. By analyzing the type and amount of VOCs the gender of the egg, and the status of an individual egg can be determined.

Electromagnetic radiation in the microwave, terahertz or the infrared range may be used to analyze VOCs. The analysis spectra may be generated using absorbance, transmittance, reflectance, or Raman spectroscopy.

In a preferred embodiment, terahertz electromagnetic radiation is used for the detection of VOCs captured in a membrane. As used herein terahertz electromagnetic radiation refers to radiation having a wavelength of between 1 mm to 0.01 mm. In a particular embodiment, terahertz radiation within the 600-750 µm range is used to determine the VOC content in a PET membrane. The electromagnetic radiation detector generates an absorption spectrum. Absorption spectra can be obtained in the frequency domain, or in the time domain and translated to frequency via Fourier transform, depending on the spectroscopic method used.

The absorption spectra is read and compared to a database via software matching algorithms. The database contains spectral fingerprints of eggs with each fingerprint representing fertility status or gender for various avian species and breeds within a species. The software matching algorithm compares the collected spectrum to the catalogued fingerprint within pre-determined confidence bounds, and identifies the gender and fertility status by determining whether or not the read spectrum falls within the error bounds of the fingerprint.

Once the status of the egg is determined, eggs of the culled sex are kicked off the line using conventional egg-sorting machinery and can be retained for sale as breaking stock in the case of eggs from layer breeds and can be sorted by gender in the case of eggs from broiler breeds among other purposes. In a similar manner, infertile eggs can be separated from fertile eggs.

In an embodiment, membranes may be recycled via application of electricity to release the VOCs from the membrane. The "cleaned" membrane is cycled back into place on the sampling apparatus. In other embodiments, the membrane can be cleaned by reversing the flow of the vacuum motor, which causes air to pass through the membrane and push the absorbed molecules from the membrane. In certain embodiments, each membrane may be used only once and then replaced by a new membrane.

Figure 1:
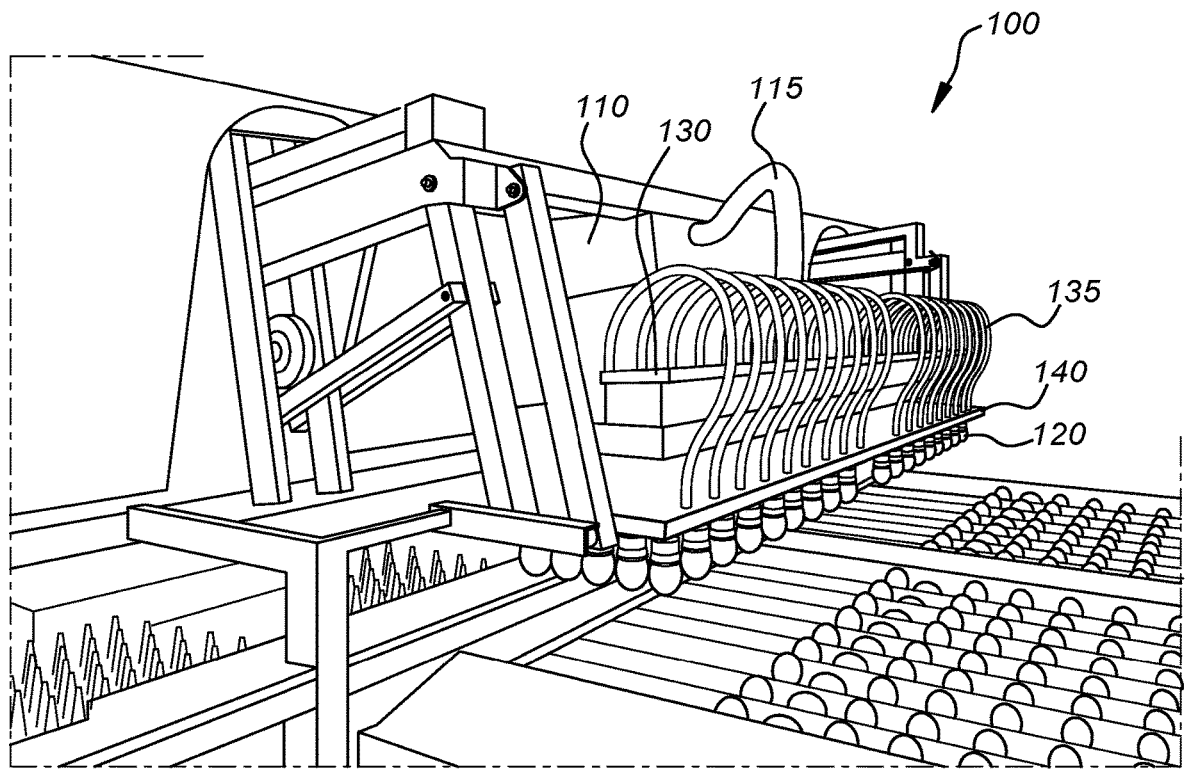
FIG. 1 illustrates an exemplary commercial vacuum egg handling system in one embodiment.

An exemplary commercial vacuum egg handling system loader (in this case, Moba FL330 loader) is depicted in FIG. 1 as an example of vacuum-handling equipment in use by a large number of hatcheries. A device similar to that shown can be used to implement the invention in a commercial setting. Incorporating a sampling apparatus into a commercial vacuum egg handling system may allow more than 100 eggs to be sampled simultaneously by the vacuum handler. Turning to FIG. 1, a vacuum egg handling system 100 generally includes a vacuum source 110 and a plurality of egg handling cups 120 coupled to the vacuum system. In an embodiment, the vacuum source 110 is coupled to the egg handling cups 120 via one or more vacuum manifolds. In the particular embodiment depicted in FIG. 1, vacuum source 110 is coupled to egg handling cups 120 via first vacuum manifold 130 and a plurality of sub-manifolds 140. As shown, vacuum source 110 is coupled to first vacuum manifold 130 via vacuum source conduit 115. First vacuum manifold 130 is coupled to a plurality of sub-manifolds 140 via a plurality of manifold conduits 135. A plurality of egg handling cups 120 are coupled to each of the sub-manifolds. The vacuum created in vacuum source 110 is conducted to each of the sub-manifolds creating a vacuum in the egg handling cup, sufficient to pull an egg into the egg handling cup and hold the egg in the egg handling cup while the egg is being transported, as shown in FIG. 1.

Figure 2:
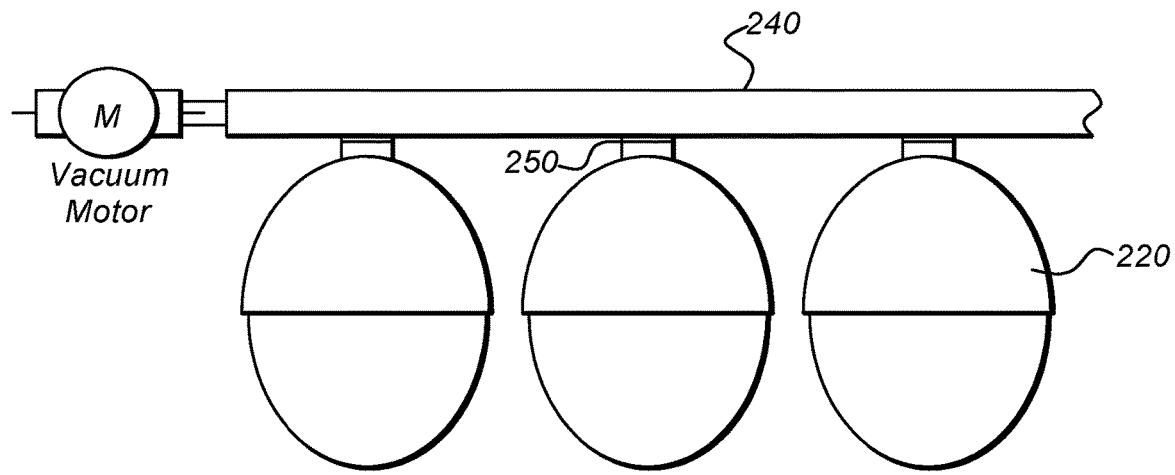
FIG. 2 depicts a schematic diagram of a sub-manifold of a vacuum egg handling system including a membrane to capture VOCs from eggs that are disposed in egg handling cups.

In one embodiment, a vacuum egg handling system, such as shown in FIG. 1, may be modified to include a plurality of sampling apparatuses. FIG. 2 depicts a schematic diagram of a sub-manifold 240 of a vacuum egg handling system that is modified to include a membrane 250 to capture VOCs from eggs that are disposed in egg handling cups 220. In this embodiment, egg handling cups 220 act as the gas collection device. Gas in the vicinity of the egg is pulled through the egg handling cups 220 into the membrane 250 where VOCs that are produced by the egg are collected. In some embodiments, membranes may be coupled to an electric system to impart a small charge to the membrane to help with adsorption/desorption of VOCs.

As depicted in FIG. 2, each egg handling cup may be associated with a single membrane. This makes it possible to analyze the VOCs emitted by each individual egg. By incorporating a tracking mechanism into the system, the position of each egg can be matched with the membrane being analyzed. Once the analysis is complete, the eggs may be separated, by reference to the tracking system, on the basis of gender and/or fertility status.

Figure 3:
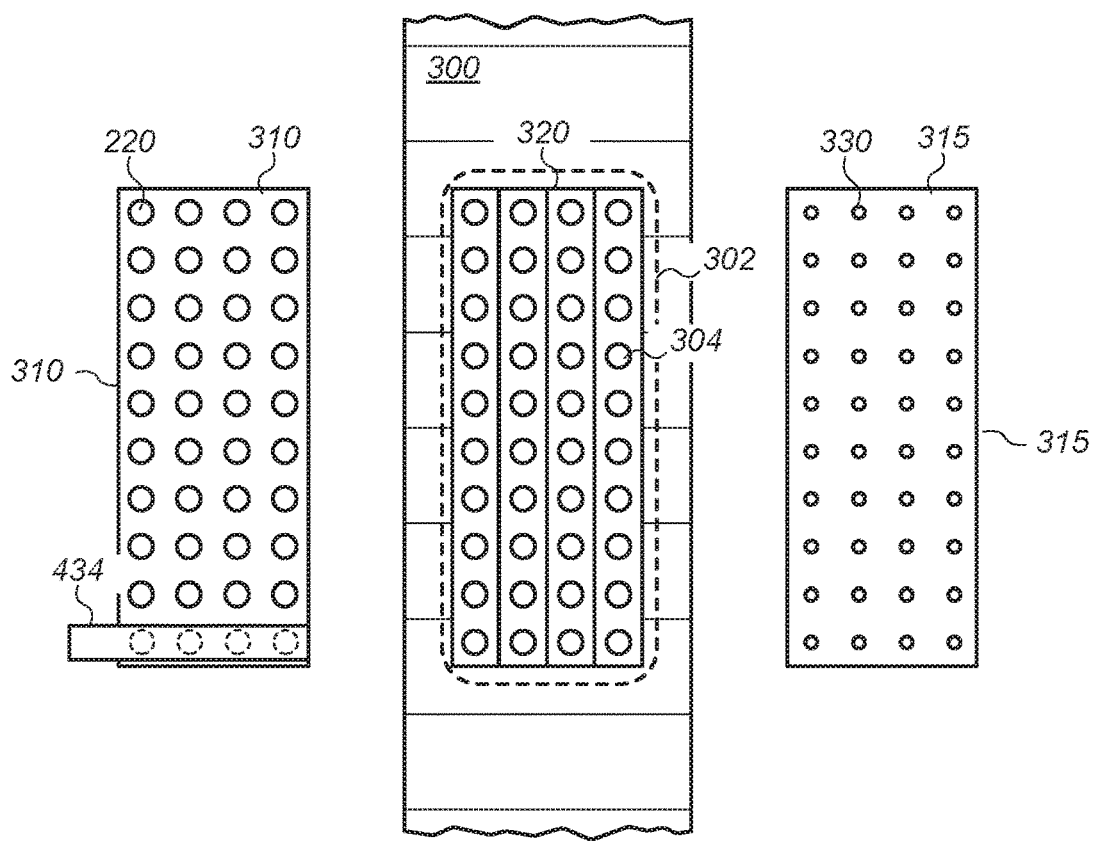
FIG. 3 is a top view illustrating an exemplary system for analyzing and sorting eggs that includes dual reading trays and a movable reading device.

An exemplary system and method of analyzing and sorting eggs is depicted in FIG. 3. In this embodiment, a conveyor has two reading trays (310 and 315) to either side, in order to enhance throughput. In an embodiment, each reading tray includes one or more electromagnetic radiation transmitters and detectors. Each reading tray may include a plurality of holes (e.g., one for each egg handling cup. The holes act as a passageway through which electromagnetic radiation (e.g., THz or IR light) can travel. In one embodiment, the egg handling cups of the vacuum egg handler, described in FIG. 2, are detachable from the vacuum handling apparatus. For example, in an embodiment, a push-activated latching system may be used to mechanically detach and reattach the egg handling cups.

Figure 4:
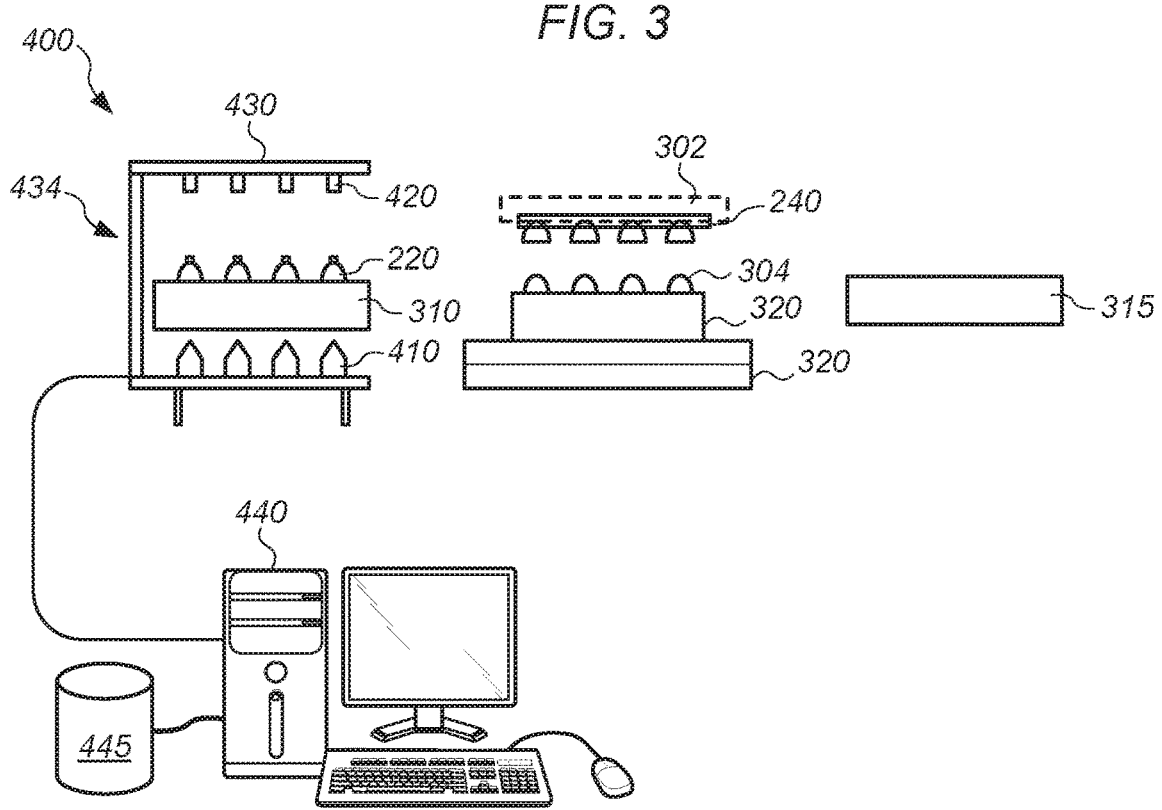
FIG. 4 is a front view illustrating an exemplary system for analyzing and sorting eggs that includes dual reading trays and a movable reading device.

The system shown in FIGS. 2, 3, and 4 may be used to determine the gender and/or fertility status of avian eggs. Initially, eggs 304 may be transferred to conveyor 300 via carrier 302. Carrier 302 is part of the vacuum handling equipment. Carrier 302 includes a sub-manifold 240 (see FIG. 4), which can be used to apply a vacuum to hold the eggs as previously described above relative to FIG. 2. The vacuum holding the eggs in place also causes VOCs to be transferred to the membranes, where the VOCs are retained. The vacuum is released and the eggs are placed in a crate 320 on the conveyor.

Carrier 302 may be coupled to a control system that controls vacuum to sub-manifolds 240. Carrier 302 is operable to selectively hold and release egg handling cups 220 and eggs, and to move egg handling cups 220 relative to the conveyor and/or reading trays. Carrier 302 may be positioned by way of motorized rail system, robotic arm, or other suitable positioning mechanism. In some embodiments, carrier 302 moves egg handling cups 220 from the conveyor to one of the reading trays and, after reading, returns the egg handling cups to the conveyor.

To read the membranes, the sub-manifold 240 and empty egg handling cups 220 are moved (e.g., via carrier 302) over to the first reading tray 310. Sub-manifold 240 is lowered, and egg handling cups 220 are released to their appropriate spots on the first reading tray 310. The egg handling cups 220 are aligned with passageways 330 (show in tray 315).

Electromagnetic radiation transmitters and detectors (e.g., terahertz or infrared electromagnetic radiation transmitters and detectors) are now used to read the detached handling cups 220. FIG. 4 depicts an embodiment of a reading system 400. Reading system 400 includes a plurality of transmitters 410, a plurality of detectors 420, and a movable frame 430 which holds the transmitters and detectors in alignment with each other. Transmitters 410, detectors 420, and a movable frame 430 may be included in reading device 434. In the embodiment depicted, the movable frame 430 may be a sliding arm guided by a track, wheels, or some other device that allows the frame to be moved along a reading tray 310. In an embodiment, frame 430 includes at least enough transmitters and detectors to read a single row of membranes disposed in the egg holding cups. In alternate embodiments, the frame may hold less than a row worth of transmitters and detectors (e.g., a single transmitter/detector pair). In such an embodiment, the movement mechanism of the frame may allow the frame to be moved in such a way that each of the membranes in egg holding cups that were placed on reading tray 310 can be read. During use, the transmitters and detectors are operated to read each of the membranes disposed in the egg holding cups. A computer system 440 is coupled to the detectors to record the spectral information collected by the detectors. The spectral information is compared to spectral information collected in database 445, which may be remotely located. This information is used to determine the gender and/or fertility status of the eggs. Computer system 440 and database 445 may be located at the facility, or at a different location (and remotely connected via, for example, a network). In one embodiment, computation relating to determination of fertility and gender and/or storage of data relating to egg spectra are accomplished remotely (e.g., through cloud services via a communication network).

The computer also includes tracking software that maps the obtained spectral information to the location of the egg on the tray. The tracking software may use bar codes or RFID on the trays (and/or pallets on which trays are held) or the egg handling cups to track the position of the eggs to the egg handling cup that captured the VOCs. After the analysis is complete, the computer will send information to the vacuum egg handling apparatus to indicate which eggs need to be removed from the conveyor based on the gender and/or the fertility status. Sorting may be accomplished by removing eggs from the vacuum egg handling device before the eggs are transferred to crate 320. Alternatively, the eggs may be sorted by placing the eggs on crate 320, then using further egg handling equipment downstream from the analysis component to separate the eggs based on gender and/or fertility status.

While reading tray 310 is being scanned, carrier 302 may move sub-manifolds 240 to reading tray 315, wherein egg handling cups that have been previously read can be reattached to the sub-manifolds. In one embodiment, reading tray 315 may be used to clean the membranes from the previously read egg handling cups. In one embodiment, after all of the egg handling cups are read, a fluid stream (e.g., air or an inert gas such as nitrogen) is passed through the passageways of reading tray 315 (or reading tray 310) that removes VOCs from the membranes. Alternatively, an electrical system may be incorporated in the reading trays so that an electrical current can be passed into the membrane to remove the VOCs. A combination of air or an inert gas and electrical current may also be used. Alternatively, membranes may be discarded and replaced with new, clean ones. In another embodiment, as the vacuum handler lifts the egg handling cups, the vacuum handler may blow air or an inert gas through the membranes (e.g., by reversing the vacuum motor), incite an electric current in the membrane, or use a combination of both methods to remove VOCs from the membrane.

After the sub-manifolds have been reloaded with the egg handling cups, the vacuum egg handling system uses the egg handling cups to obtain a new collection of eggs and place them on the conveyer. In an embodiment, the cleaning of membranes at reading tray 315 and collection of eggs is completed at about the same time that reading the membranes at reading tray 310 is completed. The cycle set forth above is repeated for each collection of eggs obtained, allowing more than 100 eggs to be sampled and tested within minutes.

Sample Chamber System

In another embodiment, a system for determining the gender and/or fertility status of avian eggs includes a sampling apparatus that can be used to collect volatile organic compounds (VOCs) from an intact egg. In one embodiment, the sampling apparatus includes a vacuum source and a sample chamber capable of holding volatile organic compounds emitted by an intact egg.

During use, a sampling apparatus applies a vacuum from the vacuum source to the gas proximate to the avian egg and directs the gas captured from the vicinity of the egg into the sample chamber. In an embodiment, the sampling apparatus includes a gas collection device which is placed proximate to the egg, as previously discussed.

Figure 5:
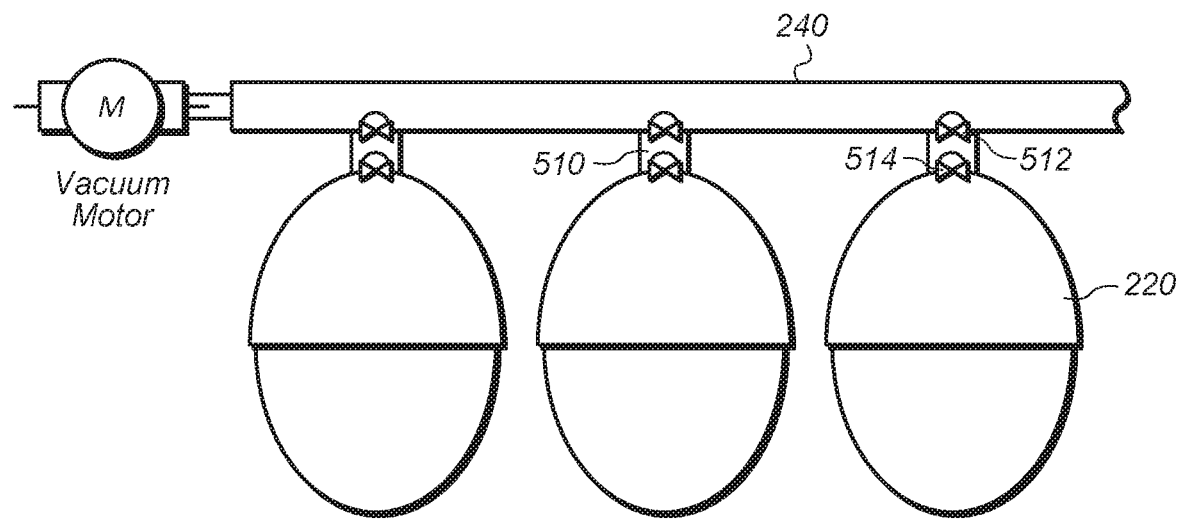
FIG. 5 depicts a schematic diagram of a sub-manifold of a vacuum egg handling system that includes a sample chamber to capture VOCs from eggs that are disposed in egg handling cups.

In one embodiment, a vacuum egg handling system, such as shown in FIG. 1, may be modified to include a plurality of sample chambers. FIG. 5 depicts a schematic diagram of a sub-manifold 240 of a vacuum egg handling system that is modified to include a sample chamber 510 to capture VOCs from eggs that are disposed in egg handling cups 220. In this embodiment, egg handling cups 220 act as the gas collection device. Gas in the vicinity of the egg is pulled through the egg handling cups 220 into the sample chamber 510. Sample chamber 510 may include a top valve 512 and a bottom valve 514. During use, a vacuum may be applied to sample chamber 510 from sub-manifold 240. While a vacuum is applied to sample chamber 510, bottom valve 514 is closed. Once an appropriate vacuum is obtained, top valve 512 is closed, creating a vacuum within sample chamber 510. The egg handling cup 220, is positioned on the eggs, and bottom valve 514 is opened. The vacuum in sample chamber 510 pulls the egg into the egg handling cup and draws any VOCs being released from the egg into the sampling chamber. After a predetermined time, or once the egg has been moved into position over a crate, bottom valve 514 is opened, breaking the vacuum to the egg as VOCs are drawn into the chamber, allowing the egg to drop into a crate, at which point valve 514 is closed, sealing the collected VOCs in the sample chamber.

Figure 7:
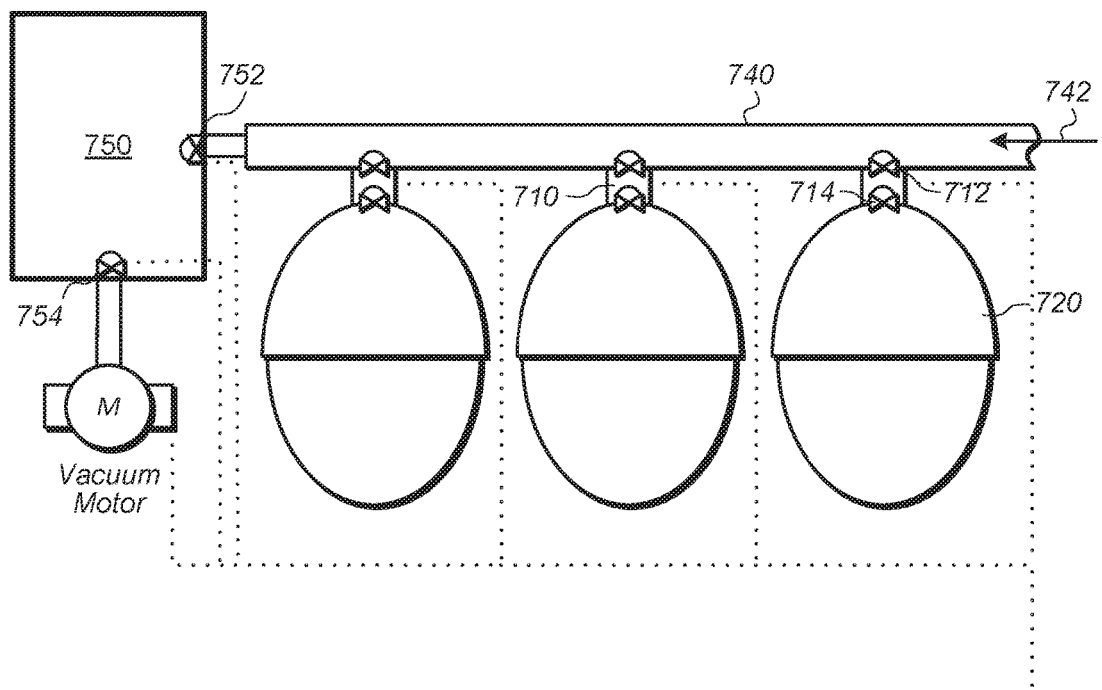
FIG. 7 depicts a schematic diagram of a sub-manifold of a vacuum egg handling system that includes a single sample chamber to analyze VOCs from eggs that are disposed in egg handling cups.

An alternate embodiment of a sub-manifold 740 of a vacuum egg handling system is depicted in FIG. 7. The sub-manifold is modified to include a sample chamber 750 which can be used to analyze VOCs captured from eggs that are disposed in egg handling cups 720. In this embodiment, egg handling cups 720, in conjunction with sample chamber 750 act as a gas collection device. Each of the egg handling cups 720 includes a top valve 712 and a bottom valve 714 which are used to define a collection space 710. Controller 760 operates the valves and the vacuum motor in sequences that allow VOCs from each egg disposed in the egg handling cups to be individually analyzed and associated with the egg.

During initial use, a vacuum may be created in collection space 710 though sub-manifold 740. The vacuum may be applied by running vacuum motor (M) so that a vacuum is created in sample chamber 750. Sample chamber 750 includes two valves, 752 and 754. Valve 752 allows gases to enter sample chamber 750 from sub-manifold 740. Valve 754 controls access of sample chamber 750 to vacuum motor (M). Initially, valves 752 and 754 are opened and the vacuum motor is operated to create a vacuum in sample camber 750 and sub-manifold 740. This also has the effect of purging both sub-manifold 740 and the sample chamber 750 of any VOCs obtained from previous tests. In an optional embodiment, a purging gas 742 may be introduced into sub-manifold 740 during evacuation of the sub-manifold and sample chamber. After a sufficient amount of purging gas is passed through the system, the purging gas is stopped and the system placed under a vacuum as discussed above. Top valves 712 are also opened, allowing a vacuum to be created in each collection space 710. Once a vacuum has been established throughout the system valves 754 and 752 are closed, creating a sealed vacuum in the sample chamber, and top valves 712 are closed creating a vacuum in each collection space 710.

During the next phase of use, egg handling cups 720, are positioned on eggs, and bottom valve 714 is opened. The vacuum in collection space 710 pulls the egg into the egg handling cup and draws any VOCs being released from the egg into the collection space.

The collected gas in each collection space is transferred to sample chamber 750 for detection of VOCs. In an embodiment, after VOCs have been collected in a collection space for a sufficient amount of time, the collected gas is transferred to sample chamber 750 by closing bottom valve 714, opening the associated top valves 712, and opening sample chamber valve 752. Sample chamber 750 is at a lower vacuum, at this time, than the rest of the system and therefore draws the collected gas into the sample chamber 750 for analysis. Once the collected gas is drawn into sample chamber 750, sample chamber valve 752 may be closed to retain the collected gas in the sample chamber. The gas in the sample chamber can be analyzed using techniques set forth herein to determine the VOC content of the gas. The VOC content of the gas is then used to determine the gender and/or fertility status of the egg in the positon associated with the collected gas. Controller 760 keeps track of the position of the egg handling cup associated with the open top valve 712 and determines where the egg should be placed to allow sorting of the egg based on gender and/or fertility of the egg.

After detection of VOCs is complete, sample chamber 750 and sub-manifold 740 are purged of the collected gas already present in the system before analyzing another egg. To purge system vacuum motor (M) is run and sample chamber valves 754 and 752 are opened allowing gas from sample chamber a 750 and the sub-manifold 740 to be pulled out of the system. During cleaning of the system a purging gas 742 may be introduced into sub-manifold 740 during evacuation of the sub-manifold and sample chamber. Once the system is purged, the above process can be repeated on other eggs attached to the sub-manifold. In this way, each egg can be identified for subsequent sorting.

Figure 8:
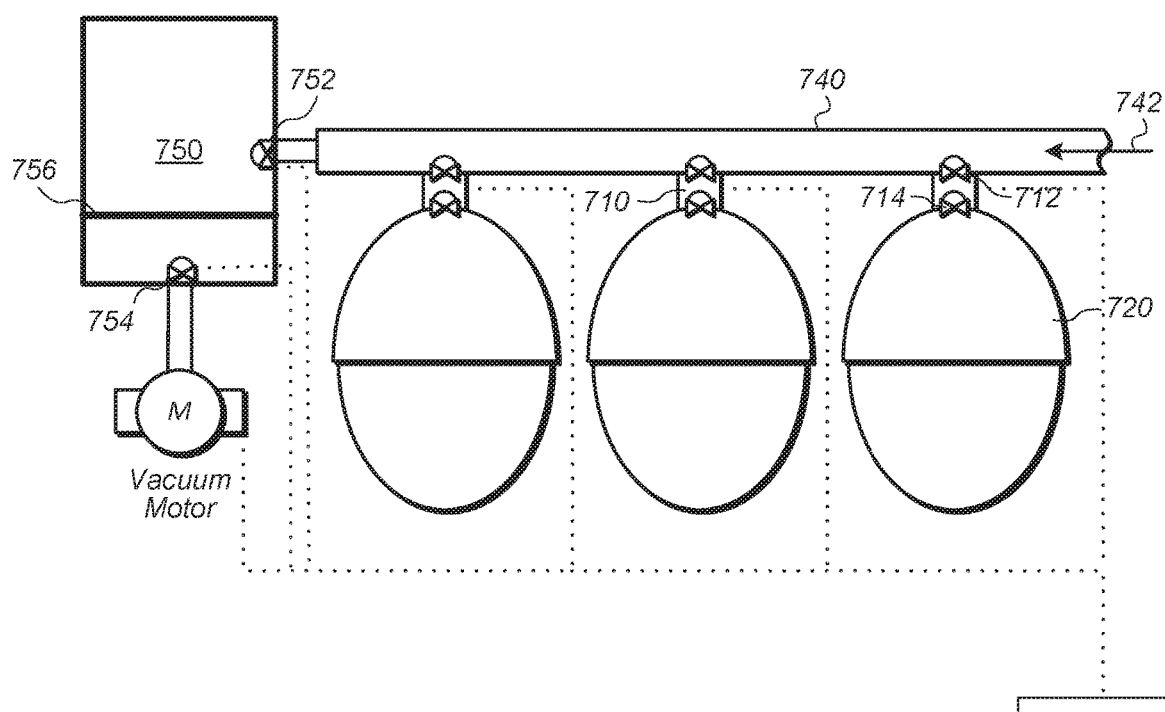
FIG. 8 depicts a schematic diagram of a sub-manifold of a vacuum egg handling system that includes a membrane sample chamber to capture VOCs from eggs that are disposed in egg handling cups.

An alternate embodiment of the system of FIG. 7 is depicted in FIG. 8. FIG. 8 is similar in many aspects to the system of FIG. 7, but differs in that sample chamber 750 includes a membrane 756 which is used to capture VOCs in the collected gas. In FIG. 8, during initial use, a vacuum may be created in collection space 710 though sub-manifold 740. The vacuum may be applied by running vacuum motor (M) so that a vacuum is created in sample chamber 750. Sample chamber 750 includes two valves, 752 and 754. Valve 752 allows gases to enter sample chamber 750 from sub-manifold 740. Valve 754 controls access of sample chamber 750 to vacuum motor (M). Initially, valves 752 and 754 are opened and the vacuum motor operated to create a vacuum in sample camber 750 and sub-manifold 740. This also has the effect of purging both sub-manifold 740 and the sample chamber 750 of any VOCs obtained from previous tests. Top valves 712 are also opened, allowing a vacuum to be created in each collection space 710. Once a vacuum has been established throughout the system top valves 712 are closed creating a vacuum in each collection space 710.

During the next phase of use, egg handling cups 720, are positioned on eggs, and bottom valve 714 is opened. The vacuum in collection space 710 pulls the egg into the egg handling cup and draws any VOCs being released from the egg into the collection space.

The collected gas in each collection space is transferred to sample chamber 750 for detection of VOCs. In contrast to the system depicted in FIG. 7, transfer of the collected gas is assisted by use of a membrane. In an embodiment, after VOCs have been collected in a collection space for a sufficient amount of time, the collected gas is transferred to sample chamber 750 by turning vacuum motor on (if the motor was turned off), opening sample chamber valves 754 and 752, and opening the top valve 712 and bottom valve 714 associated with the egg being examined. The vacuum created by vacuum motor (M) draws the collected gas from collection space 710 into sample chamber 750 and through membrane 756. As the collected gas is drawn across the membrane, VOCs emitted by the egg are captured by the membrane. Once a sufficient amount of gas associated with the egg is collected, sample chamber valves 752 and 754 may be closed to movement of gas through membrane 756. The membrane in the sample chamber can be analyzed using techniques set forth herein to determine the VOC content of the gas. The VOC content of the gas is then used to determine the gender and/or fertility status of the egg in the positon associated with the collected gas. Controller 760 keeps track of the position of the egg handling cup associated with the open top valve 712 and determines where the egg should be placed to allow sorting of the egg based on gender and/or fertility of the egg.

After analysis of membrane 756 is complete, the membrane may be cleaned or replaced as discussed above for other membrane systems. To prepare for the next reading, sample chamber 750 and sub-manifold 740 are purged of any collected gas already present in the system before analyzing another egg. To purge system vacuum motor (M) is run and sample chamber valves 754 and 752 are opened allowing gas from sample chamber a 750 and the sub-manifold 740 to be pulled out of the system. During cleaning of the system a purging gas 742 may be introduced into sub-manifold 740 during evacuation of the sub-manifold and sample chamber. Once the system is purged, the above process can be repeated on other eggs attached to the sub-manifold. In this way, each egg can be identified for subsequent sorting.

Using these systems, each egg handling cup may be associated with a single sample chamber. This makes it possible to analyze the VOCs emitted by each individual egg. By incorporating a tracking mechanism into the system, the position of each egg can be matched with the sample chamber being analyzed. Once the analysis is complete, the eggs may be separated, by reference to the tracking system, on the basis of gender and/or fertility status.

The system of FIGS. 3 and 4 may be used to analyze the VOCs collected from the eggs, in a similar manner to the method used to analyze the membrane captured VOCs. In an embodiment, the egg handling cups of the vacuum egg handler, described in FIG. 5, are detachable from the vacuum handling apparatus. The sub-manifold 240 and now empty egg handling cups are moved over to the first reading tray 310. Sub-manifold 240 is lowered and the egg handling cups are released to their appropriate spots on the first reading tray 310. The egg handling cups 220 are aligned with passageways 330. Electromagnetic radiation transmitters and detectors (e.g., terahertz, microwave or infrared electromagnetic radiation transmitters and detectors) are now used to read the sample chambers in the detached handling cups 220 in the manner described above. After the analysis is complete, the computer will send information to the vacuum egg handling apparatus to indicate which eggs need to be removed from the conveyor.

While one reading tray is being scanned, the vacuum handling machine may move the sub-manifolds to a second reading tray, where egg handling cups that have been previously read can be reattached to the sub-manifolds, effectively doubling the rate at which eggs can be read in the system. In one embodiment, each reading tray may be used to clean VOCs from the sample chambers. In one embodiment, after all of the egg handling cups are read, a stream of gas is passed through the passageways of a reading tray creating a stream of gas that removes VOCs from the sample chambers. Alternatively, as the vacuum handler lifts the egg handling cups, the vacuum handler may blow air through the sample chambers (e.g., by reversing the vacuum motor) to remove the VOCs from the sample chamber. During cleaning of the sample chamber, both valves 512 and 514 are opened.

After the sub-manifolds have been reloaded with the egg handling cups, the vacuum egg handling system uses the egg handling cups to obtain a new collection of eggs and place them on the conveyer. The cycle set forth above is repeated for each collection of eggs obtained, allowing more than 100 eggs to be sampled and tested within minutes.

Although in some embodiments described herein, a vacuum system was used to hold and/or collect gas, a system may, in various embodiments, collect and/or capture gases emitted from the egg without application of a vacuum.

Although in some embodiments described herein, gas collection devices (e.g., egg cups) are moved away from the egg, a system may, in various embodiments, measure air or other gases collected near the egg without moving the gas collection devices away from the egg.

In some embodiments, eggs may be read one after another (e.g., eggs arranged in a line sequentially on a conveyor belt system), rather than through a batch process as described in FIGS. 1-3.

In Ovo Detection System

In an alternate embodiment, the VOC content of the air cell present in avian eggs may be directly analyzed using electromagnetic radiation that is substantially transparent to the egg shell (i.e., in ovo VOC detection). For example, both terahertz and microwave electromagnetic radiation may be used for in ovo detection. In an embodiment, the appropriate transmitter and detector are placed in fixed positions with respect to the air cell. A plurality of pairs of transmitters and detectors can be used to analyze the VOC content of the air cell by moving eggs through the optical pathway between the transmitter and detector pair. The detected absorption spectrum is analyzed as discussed above, and a determination between gender and/or fertility status may be made. The analysis spectra may be generated using absorbance, transmittance, or reflectance through the egg shell.

In a first embodiment, eggs are positioned with their major axis vertically oriented in normal egg-crate-like storage containers, with the air cell positioned at the top of the egg. Electromagnetic radiation transmitters and detectors may be placed in optical communication with the air cell of the eggs. In a second embodiment, the eggs are positioned with their major axis vertically oriented, but with the air cell positioned at the bottom of the egg (closer to the ground). A specialized crate allowing line-of-sight access to the area of the egg containing the air cell is used to enable the electromagnetic detection system to analyze the air cell content. As noted previously, the egg orientation can be either way.

In one embodiment, an egg handling system, such as shown in FIG. 1, may be modified to include an in ovo detection system. FIG. 6 depicts a schematic diagram of an in ovo detection system. In this embodiment, a crate 320 of an egg handling system is modified to include one or more windows 610 which will allow preselected electromagnetic radiation (e.g., terahertz, microwave or infrared radiation) to pass through the window and into the egg. In an embodiment, crate 320 may include a plurality of egg holding cups, which are shaped such that the egg is naturally positioned with the air cell of the egg in optical alignment with the one or more windows. For example, the air cell of most eggs tends to be positioned at the wider side of the egg. The crate may be shaped such that the bottom of the egg holding cups is wider than the top to encourage proper alignment of the air cell with the window.

Each egg handling cup may be associated with a single individual egg. By incorporating a tracking mechanism into the system, the position of each egg can be matched with the egg handling cup holding the egg. Once the analysis is complete, the eggs may be separated, by reference to the tracking system, on the basis of gender and/or fertility status.

In an embodiment, the one or more pairs of electromagnetic radiation transmitters 620 and detectors 630 (e.g., terahertz, microwave or infrared electromagnetic radiation transmitters and detectors) are now used to read the air cell. In an embodiment, the transmitters and detectors may be coupled to a movable frame (not shown) which holds the transmitters and detectors in alignment with each other. The movable frame may be a sliding arm guided by a track, wheels, or some other device that allows the frame to be moved along the crate. In an embodiment, the frame includes at least enough transmitters and detectors to read a single row of eggs disposed in the egg holding cups. In an alternate embodiment, the movement mechanism of the frame may allow the frame to be moved in such a way, e.g. to any point along a two dimensional plane, that each of the air cells of eggs in the egg holding cups can be individually read. During use, the transmitters and detectors are operated to read each of the air cells disposed in the egg holding cups. A computer system is coupled to the detectors to record the spectral information collected by the detectors. The spectral information is compared to spectral information collected in database. As noted previously, a computer system and database may be located at the facility, or at a different location (and remotely connected via, for example, a network). In one embodiment, computations and/or storage for testing and/or egg management are accomplished through cloud services via a communication network. This information is used to determine the gender and/or fertility status of the eggs. After the analysis is complete, the computer will send information to the vacuum egg handling apparatus to indicate which eggs need to be removed from the conveyor.

While the system is depicted as reading through the "bottom" of the crates, it should be understood that, in an alternate embodiment, in ovo detection can be carried out by analyzing the exposed (that is, "top" or "upper") portion of the eggs disposed in the crate. In such an embodiment, it is necessary to place the egg in the crate with the air cell portion of the egg exposed so that a reading can be made without the need for a window.

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system for determining the gender and/or fertility status of avian eggs comprising:
   an egg handling system which comprises one or more carriers for receiving one or more avian eggs in one or more egg holding cups;
   one or more electromagnetic radiation transmitters capable of emitting preselected electromagnetic radiation, wherein the one or more transmitters direct the preselected electromagnetic radiation into a region of each of the one or more avian eggs; and
   one or more electromagnetic radiation detectors capable of detecting preselected electromagnetic radiation coming from said region of each of the one or more avian eggs and generating detection data for each of the one or more avian eggs,
   wherein said egg handling system is configured to define one or more optical windows with respect to said region of each of the one or more avian eggs, said region being an air cell region of the egg;
   wherein said one or more electromagnetic radiation transmitters and one or more electromagnetic radiation detectors comprise at least one pair of the electromagnetic radiation transmitter and detector in optical communication with air cells of the avian eggs, such that air cells of the eggs, disposed in the egg holding cups, are individually read, and
   wherein the electromagnetic radiation is preselected in accordance with one or more predetermined organic compounds in the air cell, said detection data for each of said one or more avian eggs being indicative of organic compound content of the air cell of said avian egg, to thereby allow extraction, from said detection of data, spectral information about a quantity of said one or more organic compounds in the air cell of the egg being indicative of the gender and/or fertility status of avian egg.

2. The system of claim 1, wherein the electromagnetic radiation is in the terahertz frequency range.

3. The system of claim 1, wherein at least one transmitter of said one or more transmitters and at least one detector of said one or more detectors are capable of substantially simultaneously transmitting the preselected electromagnetic radiation into a plurality of eggs.

4. The system of claim 1, wherein the egg handling system comprises a conveyance system for transporting eggs along a conveyor belt, wherein the carrier is coupled to the conveyor belt, and wherein the one or more transmitters and the one or more detectors are positioned such that transported eggs are brought into an optical pathway between each pair of the transmitters and the detectors.

5. The system of claim 1, wherein said one or more optical windows are positioned proximate to a location of the air cell region of the avian eggs when disposed in the carrier, wherein the one or more optical windows allow the preselected electromagnetic radiation to pass through the one or more optical windows, and wherein the transmitter is optically aligned with the window such that the preselected electromagnetic radiation emitted by the transmitter passes through the window to the air cell region of the egg.

6. The system of claim 5, wherein the carrier is movable such that the one or more optical windows can be moved into an optical pathway between one or more of each of the transmitters and the detectors.

7. The system of claim 5, wherein one or more of each of the transmitters and/or the detectors are movable such that the one or more windows can be positioned into an optical pathway between the transmitter and the detector.

8. The system of claim 5, wherein the egg holding cups are configured as egg shaped cups for holding the avian eggs in a position such that the air cell of the egg is positioned in the optical window of the carrier.

9. The system of claim 5, further comprising: a vacuum source in communication with the carrier, a gas collection device coupled to the vacuum source, and a membrane positioned in the passageway coupling the vacuum source to the gas collection device, wherein the membrane is capable of capturing volatile organic compounds, the system being configured and operable to apply a vacuum from the vacuum source to gas proximate to the avian egg and direct the gas captured from the vicinity of the egg toward the membrane; wherein the membrane is positionable within the electromagnetic radiation emitted by the one or more transmitters.

10. A method of determining the gender and/or fertility status of avian eggs, the method comprising:

providing an egg handling system which comprises one or more carriers for receiving one or more avian eggs in one or more egg holding cups;

providing one or more electromagnetic radiation transmitters capable of emitting preselected electromagnetic radiation, wherein the one or more transmitters are configured to direct the preselected electromagnetic radiation into a region of each of the one or more avian eggs; and one or more electromagnetic radiation detectors capable of detecting preselected electromagnetic radiation coming from said region of each of the one or more avian eggs and generating detection data for each of the one or more avian eggs; wherein said egg handling system is configured to define one or more optical windows with respect to said region of each of the one or more avian eggs, said region being an air cell region of the egg; said one or more electromagnetic radiation transmitters and one or more electromagnetic radiation detectors comprise at least one pair of the electromagnetic radiation transmitter and detector in optical communication with air cells of the avian eggs, such that air cells of the eggs, disposed in the egg holding cups, are individually read;

positioning the air cell of an egg in an optical pathway between the transmitter and the detector of the pair; and applying the preselected electromagnetic radiation to the air sac cell region of the egg, wherein the electromagnetic radiation is preselected to allow the quantity of one or more organic compounds in the air cell of the egg to be determined.

11. The method of claim 10, further comprising substantially simultaneously transmitting the preselected electromagnetic radiation into a plurality of eggs.

12. The method of claim 10, wherein the electromagnetic radiation is in the terahertz frequency range.

13. The method of claim 10, comprising moving the carrier along a conveyor belt such that the eggs are transported and the air cell region of the eggs are brought into the optical pathway between the one or more transmitters and the one or more detectors.

14. The method of claim 10, comprising optically aligning the one or more transmitters with the one or more optical windows such that the preselected electromagnetic radiation emitted by the one or more transmitter passes through the one or more optical windows to the air cell region of the egg.

15. The method of claim 13, further comprising moving the carrier such that the one or more optical windows are moved into the optical pathway between the one or more transmitters and the one or more detectors.

16. The method of claim 10, further comprising moving at least one of the one or more transmitters and the one or more detectors such that the one or more optical windows are positioned in the optical pathway between the one or more transmitters and the one or more detectors.

17. The method of claim 10, further comprising applying a vacuum to gas proximate to the avian egg and directing the gas captured from the vicinity of the egg toward a membrane positioned within a passageway of the electromagnetic radiation emitted by the transmitter.

\* \* \* \* \*